(12) United States Patent
Slagman et al.

(10) Patent No.: US 8,445,235 B2
(45) Date of Patent: May 21, 2013

(54) **PROCESS FOR THE PRODUCTION OF THE *ACTINOBACILLUS PLEUROPNEUMONIAE* TOXINS APXI OR APXIII IN A LIQUID CULTURE MEDIUM UNDER SUPPLY OF AIR ENRICHED IN CARBON DIOXIDE**

(75) Inventors: Simen-Jan Slagman, Boxmeer (NL); Christian Theodoor Gerardus Smits, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 84 days.

(21) Appl. No.: 13/131,121

(22) PCT Filed: Nov. 25, 2009

(86) PCT No.: PCT/EP2009/065797
§ 371 (c)(1),
(2), (4) Date: May 25, 2011

(87) PCT Pub. No.: WO2010/060916
PCT Pub. Date: Jun. 3, 2010

(65) Prior Publication Data
US 2011/0229934 A1 Sep. 22, 2011

Related U.S. Application Data

(60) Provisional application No. 61/118,766, filed on Dec. 1, 2008.

(30) Foreign Application Priority Data

Nov. 27, 2008 (EP) .................................... 08105880

(51) Int. Cl.
*C12P 21/04* (2006.01)

(52) U.S. Cl.
USPC ........... 435/71.3; 435/6.15; 435/41; 435/70.1

(58) Field of Classification Search
USPC ................................ 435/6.15, 41, 70.1, 71.3
See application file for complete search history.

(56) References Cited

U.S. PATENT DOCUMENTS 6,019,984 A 2/2000 MacInnes et al.

FOREIGN PATENT DOCUMENTS

EP 0 453 024 10/1991

OTHER PUBLICATIONS

Frey, J., et al., "*Actinobacillus pleuropneumoniae* RTX-toxins: Uniform Designation of Haemolysins, Cytolysins, Pleurotoxin and their Genes", Journal of General Microbiology, (1993) 139(8):1723-1728.
Jarma, Erica, et al., "Anaerobiosis, Growth Phase and *Actinobacillus pleuropneumoniae* RTX toxin Production", Microbial Pathogenesis, (2004) 37(1):29-33.
Kennedy, M. and Krouse, D., "Strategies for Improving Fermentation Medium Performance: A Review", Journal of Industrial Microbiology & Biotechnology, (1999) 23:456-475.
International Search Report for corresponding PCT/EP2009/065797, mailed Feb. 9, 2010.

*Primary Examiner* — Susan Hanley
*Assistant Examiner* — Nghi Nguyen

(57) ABSTRACT

The current invention pertains to a method to produce RTX-toxins ApxI or ApxIII by culturing *Actinobacillus pleuropneumoniae* bacteria in a liquid culturing medium that supports growth of the bacteria, characterized in that air is passed through the medium, wherein the air has a carbon dioxide content above normal atmospheric level to increase RTX-toxin production during the production phase of the RTX-toxins.

18 Claims, No Drawings

PROCESS FOR THE PRODUCTION OF THE ACTINOBACILLUS PLEUROPNEUMONIAE TOXINS APXI OR APXIII IN A LIQUID CULTURE MEDIUM UNDER SUPPLY OF AIR ENRICHED IN CARBON DIOXIDE

CROSS-REFERENCE TO RELATED APPLICATIONS

This application is a national stage entry under 35 U.S.C. §371 of PCT/EP2009/065797 filed on Nov. 25, 2009, which claims priority to EP application No. 08105880.2, filed on Nov. 27, 2008, and under 35 U.S.C. §119(e), to provisional application U.S. Ser. No. 61/118,766, filed Dec. 1, 2008. The content of PCT/EP2009/065797 is hereby incorporated by reference in its entirety.

The present invention concerns a method to produce RTX-toxins ApxI or ApxIII by culturing *Actinobacillus pleuropneumoniae* in a liquid culturing medium.

Porcine pleuropneumoniae, a major respiratory disease in pigs, is spread out worldwide and causes severe economic losses to the pig industry due to peracute deaths, treatment of acutely sick pigs and the delays in marketing of chronically infected animals. The etiological agent is *Actinobacillus pleuropneumoniae*. It is transmitted primarily by direct contact between animals, and the resulting infection produces a clinical course varying from peracute to chronic. The disease is primarily an infection of the respiratory tract having the clinical signs of high fever, severe respiratory distress, coughing and anorexia. The onset of the disease is rapid and morbidity and mortality are high. One of the ways to control *Actinobacillus pleuropneumoniae* (from now on also called "APP") infections is by vaccination programs. Bacterins have in the passed been used in such programs but were known for their serious side effects. Nowadays subunit vaccines based on the toxins of APP are commonly used.

APP produces so-called RTX-toxins (RTX stands for repeat-in-toxin). It is the presence of these RTX-toxins that highly contributes to the pathogenic character of this bacterium. The RTX-toxins have been extensively reviewed in the past and described in literature. As is commonly known, not all APP serotypes produce all RTX-toxins. For example, serotypes 1, 5, 9 and 11 produce ApxI and ApxII. Serotypes 2, 3, 4, 6 and 8 produce ApxII and ApxIII. Serotype 10 produces ApxI only and serotypes 7 and 12 produce ApxII only. Current commercially available vaccines against APP are based on the toxins ApxI, ApxII and ApxIII. Fairly recently it has been found that all APP serotypes produce a fourth RTX toxin, now called ApxIV (see EP 0 875 574).

It is commonly known how to produce the RTX-toxins ApxI or ApxIII by culturing *Actinobacillus pleuropneumoniae* in a liquid culturing medium. In particular, EP 0 453 024 already describes a method to produce ApxI (see "Example 2", paragraph 2 "Purification and characterisation of hemolysin", subparagraph "Methods") and ApxIII (see "Example 4", paragraph 2 "Purification and characterisation of App macrophage toxin (Mat)", subparagraph "Methods"). Note that ApxI used to be referred to as "HLY" whereas ApxIII was generally referred to as "Mat" (see Frey et al. in "J Gen Microbiol. 1993 August; 139 (8): 1723-8"). The medium must support the growth of APP bacteria. It is commonly known how to constitute a medium that supports growth of bacteria. Classical culture media were originally developed by Eagle, Ham and others in the 1950's and 60's. They found that a medium which fulfils the basic needs for growth should comprise inorganic salts, a nitrogen source (for example in the form of nitrogen containing compounds such as peptides or proteins), a carbon source and vitamins. The media are advantageously buffered to prevent them from becoming either too acidic or too alkaline. Within this basic recipe, many different constitutions are available. For example, one could opt for animal derived components to provide the amino acids, but one could also choose for chemically defined amino acids. For the other compounds also numerous variations are possible. Indeed, to constitute a medium that supports growth of bacteria is relatively simple. However, optimisation of growth and/or metabolite production can take some development time, in particular when a medium is preferred that is free of serum or other animal derived components. Strategies for improving fermentation medium performance however are commonly known in the art and elaborately described in literature (see for example a review article by Kennedy and Krouse in the Journal of Industrial Microbiology & Biotechnology (1999) 23, 456-475). Such optimisation forms part of the routine experiments within a fermentation laboratory. In case of cultivation of APP, NAD (nicotinamide adenine dinucleotide) inherently forms part of the medium since APP is NAD dependent. Without NAD, a medium will not support growth of the *Actinobacillus pleuropneumoniae* bacteria and can thus not be considered as a liquid medium for supporting growth of APP in the sense of the present application and the appended claims. Liquid media for supporting growth of bacteria, or components to constitute such media, are commercially available from various companies such as Sigma Aldrich, Quest International, Oxoid, Becton Dickinson, Pharmacia, VGD Inc, Mediatech, Invitrogen, Marcor, Irvin Scientific etc.

Although the prior art provides methods to produce the RTX-toxins ApxI and ApxIII by culturing APP, there is a need for improvement of the production yield. Up to date, attempts to improve the production yield mainly aimed at the production rate of the toxins in the stationary phase of the cultivation of APP, since it is known that maximum RTX-toxin production takes place at high cell densities, thus at the end of the exponential growth phase (see e.g. Microbial Pathogenesis 37 (2004) 29-33). These attempts have not led to significant improvement of the overall production yield. Surprisingly however, applicant found that when air is passed through the medium during the production phase (thus during the growth and/or stationary phase of the APP bacteria) of the said RTX-toxins of *Actinobacillus pleuropneumoniae*, wherein the air has a carbon dioxide content above normal atmospheric level, the RTX-toxin production is significantly increased. Indeed, it is generally known to use an increased carbon dioxide level during the culturing of colonies of bacteria on plates (see e.g. U.S. Pat. No. 6,019,984: EXAMPLES "Bacterial Strains and Growth Conditions"). However, this concerns the culturing of colonies of bacteria, which bacteria are then used for inoculating fermentors. At this stage, only the growth of the bacteria themselves takes place, production of RTX toxins does not (at least not at a significant level). As soon as the APP bacteria are brought over in a liquid medium to grow towards high cell densities suitable for RTX toxin production, prior art teaches to dispense with the increased carbon dioxide level. This of course is in line with the prior art teaching mentioned hereabove that the maximum Apx production in fermentors takes place only at high cell densities, thus at the end of the exponential growth phase. At this stage, cell growth has ended and plays no roll at all, and thus carbon dioxide has previously been considered as not being significant. Moreover, APP bacteria themselves produce carbon dioxide while forming the RTX-toxins. Thus, purposively adding carbon dioxide to the medium is believed to even suppress toxin production. These facts explain why carbon dioxide has never been recognized as a stimulating factor for the RTX-toxin production yield. The reason however why carbon dioxide does stimulate the production of ApxI and ApxIII is not clear, especially since carbon dioxide seems to have no positive effect on the production level of the RTX-toxin ApxII.

It is noted that many techniques exist that enable the passing of air through the medium. A commonly used concept is to pass the air via a device that lets the air escape somewhere in the medium (i.e. under the surface of the medium) in the form of bubbles. Such devices may have one single nozzle or a multitude of nozzles, depending i.a. on whether or not one wants to establish a (near) equilibrium situation in the medium and if so, how fast this equilibrium should settle. In any case, passing air through the medium is in contrast with using a head space of air and simply rely mainly on diffusion. Such a technique has been found to provide inadequate results. "Air" in the context of the present invention means a gaseous medium comprising one or more gaseous components that are normally present in atmospheric air such as oxygen, nitrogen, carbon dioxide, helium, neon, argon, xenon, radon etc. A "normal atmospheric level for carbon dioxide" is 0.04% volume $CO_2$ over the total volume of air."

In an embodiment the air is passed during the exponential growth phase of the *Actinobacillus pleuropneumoniae* bacteria. The exponential growth phase, in contrast what has been described in the prior art, appears to be a phase that is part of the overall production phase of the RTX-toxins (next to the stationary phase). Surprisingly, applicant found that passing carbon dioxide during the exponential growth phase provided a very significant stimulating RTX-toxin production, such that even at the end of this phase an economically relevant amount of toxin is present in the fermentor. Therefore, this embodiment provides the option to end the fermentation at the end of the exponential growth phase or early in the stationary phase. An important advantage is that it may save significant production time and also, that the amount of lipopolysaccharides in the end product may be reduced.

In another embodiment, wherein the medium is buffered (i.e. a substance is added that minimises a change in the acidity of a solution when an acid or base is added to the solution), it is buffered by using a bicarbonate (i.e. a salt containing $HCO_3^-$ ions). By using a bicarbonate buffer, it appears that the inherent pH lowering effect of the excess carbon dioxide can be counteracted very effectively. Apparently, using such a buffer, for example sodium bicarbonate or another alkali metal bicarbonate buffer, a (near) equilibrium state will almost be instantly reached in the medium.

In yet another embodiment the air is passed through the medium via a constant flow. Indeed, many different ways of passing gas through the medium can be devised. A pulsating flow with air having an extreme high carbon dioxide content (up to for example 90%) is one of them. However, we found that with a constant flow, very good results can be obtained. With such a constant flow, moderate carbon dioxide levels can be used in the air. This provides the advantageous effect that the buffer will be better capable of keeping the pH around the equilibrium value at any time. Note that a constant flow does not necessarily mean that overall, the carbon dioxide addition is not interrupted at some points in time. For example, a short interruption of the flow during cultivation does not exclude that before and after that interruption, the flow is constant. In an embodiment, the air is passed continuously during the exponential growth phase of the *Actinobacillus pleuropneumoniae* bacteria, i.e. during the exponential growth phase the flow will not be interrupted.

In an embodiment the carbon dioxide content is up to 10% v/v. In this embodiment, the maximum volumetric content of the carbon dioxide in the air is 10%. Above this level, it is likely that the buffer will not be able to provide equilibrium at all times at a high speed. This may negatively influence the RTX-toxin production yield. In a preferred embodiment the carbon dioxide content is 5% v/v. Good results have been achieved with this carbon dioxide content and also, from an economical point of view this is the preferred amount of carbon dioxide since such mixture is commercially available at very low prices.

In an embodiment wherein the RTX-toxin is ApxI, the culturing medium contains calcium borogluconate. Indeed, it is commonly known that the transcriptional activity of the ApxI operon is enhanced by addition of calcium to the growth medium (see: Microbiol Pathogenesis 37 (2004) 29-33). Several advantages have been found when using borogluconate (2,3-dihydroxy-3-[2-hydroxy-5-(hydroxymethyl)-1,3,2-dioxaborolan-4-yl]propanoate) to complex the calcium ions. Firstly, it appears that the generally encountered problem of precipitated calcium salts in down stream processing, in particular filters that tend to become silted, can be prevented or at least significantly reduced. Next to this, it appears that one can produce ApxI at a level that is significantly increased when compared with prior art methods that use other complexing agents such as EDTA. Apparently, by using this particular complexing agent, such that the medium contains the complex calcium borogluconate (i.e. calcium 2,3-dihydroxy-3-[2-hydroxy-5-(hydroxymethyl)-1,3,2-dioxaborolan-4-yl] propanoate, also known as D-Gluconic acid, cyclic 4,5-ester with boric acid, calcium salt 2:1) substantial precipitation of the calcium ions with other negative ions can be prevented, while at the same time the calcium ions are still available for enhancing the transcriptional activity of the ApxI operon of *Actinobacillus pleuropneumoniae*.

Although not essential for the present invention, the medium may be free of animal derived components. A disadvantage of many prior art methods is that they rely on the use of media containing animal derived components such as Columbia broth. Other animal derived components mentioned in the prior art are for example Columbia Broth Modified or Brain Heart Infusion broth. As is commonly known, the use of animal components has some severe drawbacks. First of all, the chemical composition may vary considerably between production lots. Also, supplements of animal origin may be contaminated with infectious agents. A major fear is the presence of prions causing TSE in humans or animals. One could simply opt for a medium that is free of animal components (often referred to as an "ACF"-medium). "Animal component" in this sense means any component that is present as such in an animal (for example, blood or a protein) or derived from such a component (for example modified serum derived from the blood, or amino acids derived from the protein). Applicant however found that the ApxI production efficiency is far lower when such ACF media are used when compared to media containing animal derived components, even when the calcium concentration is at a sufficient level. Without being bound to theory, it may be that with the use of serum, the problem with calcium salt precipitation is not so severe due to the presence of agents that form soluble complexes of the calcium ions. In any case, when borogluconate is used to complex the calcium ions, significant ApxI yield increase can be obtained, surprisingly resulting in a yield that is even higher than a yield obtainable with a traditional serum containing medium.

MATERIALS EN METHODS

Bacterial Strain and Media

The studies were performed using an ApxI producing *Actinobacillus pleuropneumnoiae* strain, serotype 10, hereafter called APP 10, and a strain producing ApxII and ApxIII, viz. a strain of serotype 2, here-after called APP 2. In all cases, working seeds of these strains were reconstituted using Columbia Blood Agar BASE (BAB) plates (available from Becton, Dickinson USA). Liquid media used were either Columbia broth (available from Becton, Dickinson USA) or an animal component free medium (called "ACF"). The latter medium contained as a buffer a mixture of $K_2HPO_4$ (14.6 g/l) and $NaH_2PO_4$ (3.6 g/l), and next to this $NaNO_3$ (0.2 g/l), 50% glucose solution (10 ml), yeast extract 15 g/l (available from Becton Dickinson) tracer elements (e.g. 2.5 ml of solution SL-10 as mentioned in the Handbook of Microbiological Media, 3rd edition, Ronald Atlas, CRC Press, 2004), and a 10 mM amino acids solution (containing all 20 amino acids, except tryptophan). An alternative animal component free medium tested (called "ACF-alt") contained cysteine.HCl (0.1 g/l), $NaNO_3$ (0.5 g/l), KCl (0.1 g/l), tracer elements (as above), 50% glucose solution (10 ml) and a 10 mM amino acids solution (as above), HEPES buffer (6 g/l; e.g. available from Sigma Aldrich) and yeast extract (10 g/l).

These media were used in precultures and in fermentations. Nicotinamide Adenine Dinucleotide (0.01%) was used in precultures and fermentations. All media were sterilized by 0.22 μm filtration. Prior to utilization in fermentations, the media were heated at 85° C. for one minute.

Cultivation

Preculture

Working seeds of the APP strains were plated out on a Columbia BAB plate and incubated during approximately 24 hours at 37° C. Several colonies were picked to inoculate 500 mL bottles containing 75 ml Columbia broth. The bottles were incubated during approximately 6 hours at 37° C. under agitation to form a preculture. With these precultures several fermentations were carried out.

Cultivation in SIXFORS Fermentor

In a SIXFORS fermenter (Infors AG, Switzerland) containing approximately 400 mL culture medium, about 20 mL of the preculture was added as inoculum. Cultivation temperature is 37° C., pH=7.2±0.1 (through addition of 4N sodium hydroxide or 4N acetic acid), and aereation is at 50% $pO_2$. The fermenter culture was stopped after about 24 hours Cultivation in Biostat Fermentor In a Biostat C fermenters (B. Braun Biotech, Germany), which contained 10 L medium, 500 mL of APP preculture was added as inoculum. The same settings were applied as in the SIXFORS fermentors. However, carbondioxide level was increased by maintaining a constant airflow of 1 vvm (=volume gas per volume medium per minute) for an air/$CO_2$ 95/5 v/v gas mixture. This results in aeration settings having a $pCO_2$ of about 5%. The fermenter culture was stopped at the end of the exponential phase, after approximately 8.5 hours.

Cultivation at Pilot Plant Scale

Pilot plant experiments were carried out in a 100 l batch sterilisable fermentor. Stirrer axes were equipped with three six-bladed Rushton turbine impellers. The fermentor was filled with 75 liter medium and inoculated with 3 liter preculture. Temperature was kept at 37° C., pH at 7.3 by an automatic pH controller using 20% (w/v) NaOH and 8 N acetic acid. Standard cultivation was performed under a $CO_2$ headspace over-pressure (500 mbar) and the impellers were rotated at a constant speed of 250 rpm. Oxygen pressure was not controlled. For the sparged $CO_2$ cultivation experiments the medium was supplemented with $NaHCO_3$ to a final concentration of 10 mM and aerated with a constant airflow of 0.25 vvm air enriched with 0.014 vvm $CO_2$. This leads to a $PCO_2$ of about 5%. In case of the APP 10 strain, the medium was supplemented with 25 mM $CaCl_2$ and aereation was at 50% $pO_2$ Analysis At the end of each experiment, samples of the bacterial cell cultures were aseptically taken from the fermentor to determine the optical density at 648 nm and the ApxI, ApxII and/or ApxIII level (ELISA; Units per ml) and optionally the LPS level (LAL assay; Units*$10^5$ per ml).

Results

A first experiment was carried out at pilot plant scale with strain APP 2, to study the effect of carbon dioxide passed through the medium ("sparged" $CO_2$ experiments). The medium used was Columbia broth. Results are depicted in Table 1. The results of two experiments (exp 1 and exp 2) are given.

TABLE 1

| Cultivation method | Time (h) | $OD_{648}$ | ApxII | ApxIII | LPS |
|---|---|---|---|---|---|
| Standard, exp1 | 12 | 1.35 | 44 | 130 | 0.36 |
| Standard, exp 2 | 11 | 1.47 | 77 | 146 | 0.32 |
| Sparged $CO_2$, exp 1 | 5 | 1.42 | 52 | 242 | 0.34 |
| Sparged $CO_2$, exp 2 | 5 | 1.86 | 38 | 287 | 0.09 |

From these results it becomes clear that the ApxIII production yield can be almost doubled by passing carbon dioxide through the medium at a level above normal atmospheric pressure. No absolute increase was observed with respect to the ApxII level. The LPS concentration at the end of the exponential growth phase (which was the end of each experiment of Table 1) did not differ tremendously. But since the ApxIII level is twice as high, the amount of LPS per dose of ApxIII in an end product will be, at maximum, about half of that of the product obtained with standard settings.

A second experiment was carried out also at pilot plant scale, but now with strain APP 10, to study the effect of carbon dioxide passed through the medium ("sparged" $CO_2$ experiments) on the production of ApxI. The medium used was Columbia broth. Results are depicted in Table 2. Again, the results of two experiments (exp 1 and exp 2) are given.

TABLE 2

| Cultivation method | Time (h) | $OD_{648}$ | ApxI | LPS |
|---|---|---|---|---|
| Standard, exp1 | 12 | 2.99 | 520 | 4.10 |
| Standard, exp 2 | 11 | 3.11 | 643 | 6.10 |
| Sparged $CO_2$, exp 1 | 6 | 3.08 | 1074 | 3.36 |
| Sparged $CO_2$, exp 2 | 5 | 2.99 | 1774 | 5.48 |

As becomes clear from Table 2, for ApxI comparable results can be obtained.

In a third experiment the effect of carbon dioxide passed through the medium was studied using the ACF medium as described here-above. A first cultivation was carried out in a SIXFORS fermentor without extra carbon dioxide being passed through the medium. A second cultivation was carried out in a Biostat C fermentor, with extra carbon dioxide passed through the medium as indicated here-above. Due the fact that in a Biostat fermentor conditions can be controlled somewhat better, it was expected that the Apx toxin yield would, all things being equal, be about 2 times higher (3 times at maximum) than in the SIXFORS fermentor. Results are depicted in Table 3.

TABLE 3

| Cultivation method | Time (h) | OD$_{660}$ | ApxIII |
|---|---|---|---|
| ACF, no sparged CO$_2$ | 7 | 4.00 | 1003 |
| ACF, sparged CO$_2$ | 4.75 | 3.13 | 4575 |

Since the level of the ApxIII in the Biostat fermentor is about 4½ times as high, it may be concluded that carbon dioxide led through the medium has a positive effect on Apx production yield, also when an ACF medium is being used.

In a fourth experiment, carried out in a SIXFORS fermentor with strain APP 10, we investigated whether or not we could add the calcium in the form of a borogluconate complex (instead of uncomplexed calcium). The borogluconate concentration was varied between 40, 50 and 70 mM. Cultivation was stopped at the end of the exponential growth phase. The results are depicted in Table 4.

TABLE 4

| Cultivation method | ApxI |
|---|---|
| ACF-alt, no calcium added, 5% CO$_2$ | 0 |
| ACF-alt, 40 mM Ca-borogluconate added, 5% CO$_2$ | 520 |
| ACF-alt, 50 mM Ca-borogluconate added, 5% CO$_2$ | 357 |
| ACF-alt, 70 mM Ca-borogluconate added, 5% CO$_2$ | 222 |

From the results it can be concluded that calcium may be present in the form of a calcium-borogluconate complex to obtain sufficient levels of ApxI. The advantage hereof is that calcium precipitates do no longer negatively influence down stream processing of the medium (in particular filtering action). Higher concentrations of the borogluconate appear to negatively influence the production yield.

The invention claimed is:

1. A method to produce repeat in toxin (RTX-toxins) ApxI or ApxIII comprising culturing *Actinobacillus pleuropneumoniae* bacteria in a liquid culturing medium that supports growth of the bacteria, characterised in that air is passed through the medium during the production phase of the RTX-toxins, wherein the air has a carbon dioxide content of up to 10% v/v.

2. The method according to claim 1, characterised in that the air is passed during the exponential growth phase of the *Actinobacillus pleuropneumoniae* bacteria.

3. The method according to claim 1, wherein the medium is buffered by using a bicarbonate.

4. The method according to claim 1, characterised in that the air is passed through the medium via a constant flow.

5. The method according to claim 4, characterised in that the air is passed continuously during the exponential growth phase of the *Actinobacillus pleuropneumoniae* bacteria.

6. The method according to claim 1, characterised in that the carbon dioxide content is 5% v/v.

7. The method according to claim 1, wherein the RTX-toxin is ApxI, characterised in that the culturing medium contains calcium borogluconate.

8. The method according to claim 2, wherein the medium is buffered by using a bicarbonate.

9. The method according to claim 8, characterised in that the air is passed through the medium via a constant flow.

10. The method according to claim 9, characterised in that the air is passed continuously during the exponential growth phase of the *Actinobacillus pleuropneumoniae* bacteria.

11. The method according to claim 10 characterised in that the carbon dioxide content is 5% v/v.

12. The method according to claim 2, characterised in that the carbon dioxide content is 5% v/v.

13. The method according to claim 11, wherein the RTX-toxin is ApxI, characterised in that the culturing medium contains calcium borogluconate.

14. The method according to claim 3, characterised in that the air is passed through the medium via a constant flow.

15. The method according to claim 14 characterised in that the carbon dioxide content is 5% v/v.

16. The method according to claim 15, wherein the RTX-toxin is ApxI, characterised in that the culturing medium contains calcium borogluconate.

17. The method according to claim 5 characterised in that the carbon dioxide content is 5% v/v.

18. The method according to claim 17, wherein the RTX-toxin is ApxI, characterised in that the culturing medium contains calcium borogluconate.

* * * * *